United States Patent
Pietkiewicz et al.

(10) Patent No.: US 9,074,017 B2
(45) Date of Patent: Jul. 7, 2015

(54) PURE ALBUMIN AND ITS METHOD OF PREPARATION AND DETECTION

(75) Inventors: Jadwiga Pietkiewicz, Wroclaw (PL); Agnieszka Szydelko, Dzierzoniow (PL); Katarzyna Dzierzba, Jelenia Gora (PL); Regina Danielewicz, Wroclaw (PL); Magdalena Staniszewska, Wroclaw (PL); Arkadiusz Bartys, Legnica (PL); Andrzej Gamian, Wroclaw (PL)

(73) Assignee: Wroclawskie Centrum Baden EIT+SP Z O.O., Wroclaw (PL)

( * ) Notice: Subject to any disclaimer, the term of this patent is extended or adjusted under 35 U.S.C. 154(b) by 0 days.

(21) Appl. No.: 14/116,680

(22) PCT Filed: May 6, 2012

(86) PCT No.: PCT/IB2012/000887
§ 371 (c)(1),
(2), (4) Date: Apr. 1, 2014

(87) PCT Pub. No.: WO2013/050830
PCT Pub. Date: Apr. 11, 2013

(65) Prior Publication Data
US 2014/0205839 A1    Jul. 24, 2014

(30) Foreign Application Priority Data

May 6, 2011    (PL) .......................................... 394784

(51) Int. Cl.
*G01N 21/49*    (2006.01)
*C07K 14/765*    (2006.01)

(52) U.S. Cl.
CPC ......... *C07K 14/765* (2013.01); *Y10T 428/2982* (2015.01); *G01N 21/49* (2013.01)

(58) Field of Classification Search
None
See application file for complete search history.

(56) References Cited

FOREIGN PATENT DOCUMENTS

| EP | 0828759 B1 | 1/2001 |
|----|------------|--------|
| WO | 99/62936 A1 | 12/1999 |
| WO | WO 99/62936 A1 | 12/1999 |

OTHER PUBLICATIONS

Squire et al. "The hydrodynamic properties of bovie serum albumin monomer and dimer" Biochemistry (1968) 7, 4261-4272.*
Written Opinion of the International Searching Authority issued Nov. 6, 2013 in connection with PCT International Application No. PCT/IB2012/000887.
International Preliminary Report on Patentability issued Nov. 12, 2013 in connection with PCT International Application No. PCT/IB2012/000887.
International Search Report issued Jan. 23, 2013 in connection with PCT International Application No. PCT/IB2012/000887.
Communication Pursuant to Rules 161(1) and 162 EPC issued by the European Patent Office on Dec. 18, 2013 in connection with European Patent Application No. 12730029.1.
Response to Dec. 18, 2013 Connunication Pursuant to Rules 161(1) and 162 EPC filed with the European Patent Office on Jun. 18, 2014 in connection with European Patent Application No. 12730029.1.
Invitation Pursuant to Rule 70b(1) EPC issued by the European Patent Office on Aug. 5, 2014 in connection with European Patent Application No. 12730029.1.
Response to Aug. 5, 2014 Invitation filed with the European Patent Office on Aug. 20, 2014 in connection with European Patent Application No. 12730029.1.
Hushcha I wsp., Talanta, 2000; 53; 29-34.
Navarra, G. et al. "Influence of metal ions on thermal aggregation of bovine serum albumin: Aggregation kinetics and structural changes", Journal of Inorganic Biochemistry, Elsevier Inc., U.S., vol. 103, No. 12. Dec. 1, 2009, pp. 1729-1738.
Staniszewska Magdalena et al. "Advanced glycation end-products prepared in solution under high pressure contain epitopes distinct from those formed in the dry reaction at high temperature", Archivum Immunologiae et Therapiae Experimentalis, Birkhaeuser Verlag AG, CH, vol. 53, No. 1. Jan. 1, 2005, pp. 71-78.
Navarra G. et al., "Influence of metal ions on thermal aggregation of bovine serum albumin: Aggregation kinetics and structural changes", Journal of Inorganic Biochemistry, Elsevier Inc, US, vol. 103, No. 12, (2009) pp. 1729-1738.
Squire P G et al., "The hydrodynamic properties of bovine serum albumin monomer and dimer", Biochemistry, American Chemical Society, US, vol. 7, No. 12, (1968) pp. 4261-4272.
Staniszewska Magdalena et al., "Advanced glycation end-products prepared in solution under high pressure contain epitopes distinct from those formed in the dry reaction at high temperature", Archivum Immunologiae et Therapiae Experimentalis, Birkhaeuser Verlad AG, CH, vol. 53, No. 1, (2005) pp. 71-78.
International Search Report issued by the International Searching Authority (ISA/O.E.P.M.) on Jan. 11, 2013 in connection with International Application No. PCT/IB2012/000887.

* cited by examiner

*Primary Examiner* — Suzanne M Noakes
*Assistant Examiner* — Gerard Lacourciere
(74) *Attorney, Agent, or Firm* — Gary J. Gershik; Cooper & Dunham LLP

(57) ABSTRACT

The subject of the present invention is a pure monomeric bovine serum albumin, a method of producing it characterised by the use column chromatography in resin and a method of identifying it using dynamic light scattering.

8 Claims, 3 Drawing Sheets

A)

B)

C)

A)

B)

PURE ALBUMIN AND ITS METHOD OF PREPARATION AND DETECTION

Figure 1:
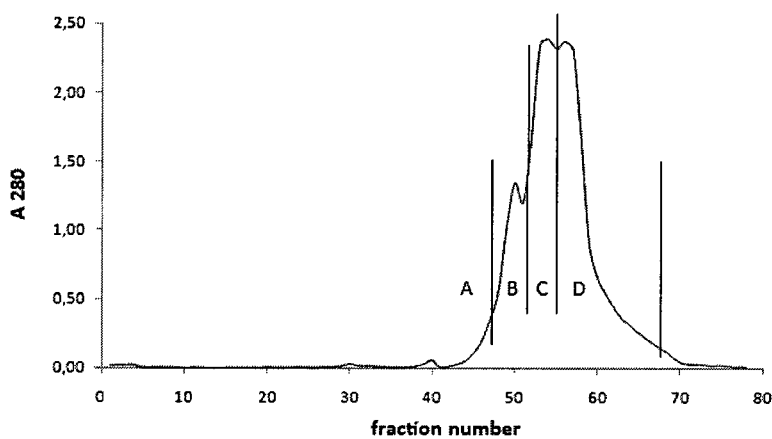
Figure 1:
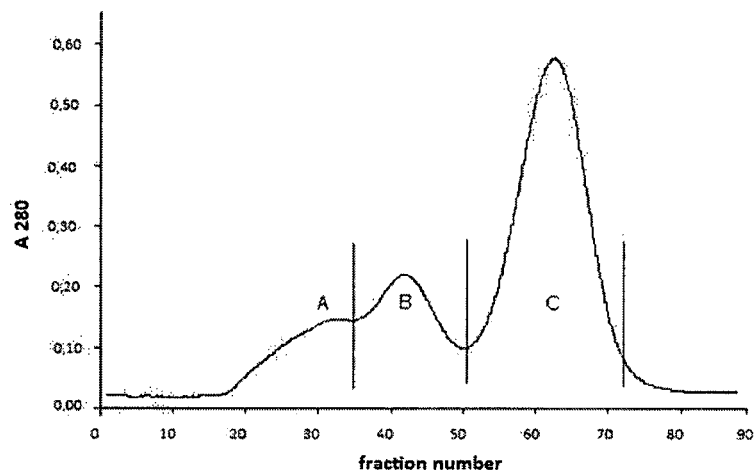
Figure 1:
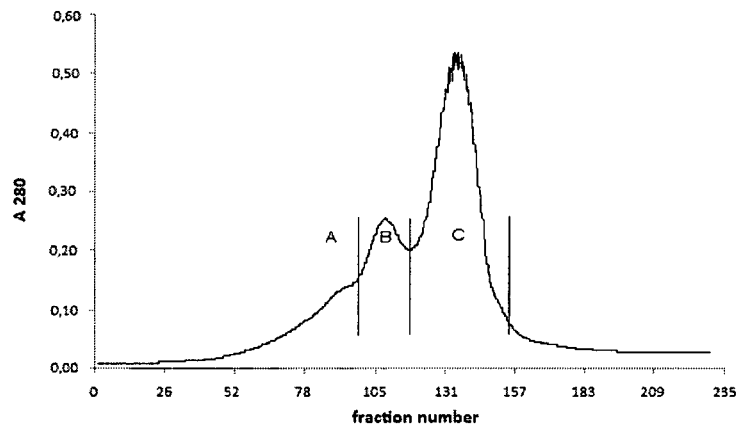

This application is a §371 national stage of PCT International Application No. PCT/IB2012/000887, filed May 6, 2012, designating the United States and claiming priority of Polish Patent Application PL 394784, filed May 6, 2011, the contents of all of which are hereby incorporated by reference into this application.

Bovine serum albumin (BSA) is one of the least expensive, commercially available proteins. It is widely used as a model protein in pure research [1-4] and a number of practical uses [5-18]. A mixture of free amino-acids obtained from BSA hydrolysis is commonly used to determine the amino-acid content of proteins. Commercial BSA used for this purpose is sufficiently pure, despite the possibility of contamination with sugars. As a result of hydrolysis, contaminants are degraded and do not hinder amino-acid analysis. Albumin is a transporter of fatty acids and other hydrophobic substances in the circulatory system. Prior to using BSA in research, it is thus worthwhile to remove hydrophobic contaminants using charcoal. BSA is used in the detection of GFP (Green Fluorescent Protein) facilitating the ultrasensitive imaging of evaluated cells [6]. Modified BSA surface-conjugated with quantum dots has been used in the analytical detection of metal ions [7]. Because this protein has turned out to be an effective carrier of photosensitizers in photodynamic therapy, it may be used as a transporter of active components in the therapy of inflammation and neoplasms [9-12]. Furthermore, as a carrier of small molecules, BSA increases the immunogenicity of the attached compounds which makes it possible to obtain highly sensitive and specific antibodies for detecting small molecules in ELISA tests [13,14]. BSA is also used in the construction of conjugated vaccines. After binding to polysaccharide antigens, it is possible to obtain effective and safe vaccines against pathogens. In a similar system, BSA is also used in neoplasm therapy [15-18]. In such uses, BSA should have a high degree of purity. In particular, it should lack carbohydrate contamination. Earlier reports indicate the presence of high molecular weight derivatives in BSA preparations [19]. Highly polymerized aggregates may form as a result of the reaction of the protein with reactive carbonyl compounds by way of glycation [20-23]. The risk of the formation of such contaminating aggregates is possible due to the presence of reducing sugars in the protein environment. A series of reports show that the protein is glycated by fructose, glucose, galactose, lactose and dextran during thermal modification under dry conditions and in dry powder formulations [24-27]. Fischer et al. analyzed the glycation products of various therapeutic monoclonal antibodies during their storage in formulations containing a buffer with sugar components and following a short incubation of these proteins with dextrose in infusion bags, commonly used in clinical practice for administering therapeutic proteins [28]. Natural glycation of commercial BSA has been observed [19]. Albumin is easily glycated in vivo as the most common serum protein [29, 30]. Aggregation has also been observed during the reaction of BSA with aldohexoses during high-temperature synthesis in dry conditions [31]. Advanced glycation products have been detected following the incubation of BSA with glucose and fructose [25,29,31,32]. GLC-MS analysis of saccharide-contaminated commercial BSA preparations has shown the presence of aldithiol acetates, demonstrating the presence of mannose, glucose and galactose in the molar ratio 1:1.6:1, respectively. The occurrence of galactose in BSA after its incubation with lactose was described in an earlier report [26]. Various methods are known of isolating proteins, making use of protein molecule size [19], surface charge [33], and in the affinity for a given carrier [34]. There are no known methods of isolating pure monomeric albumin from commercial BSA preparations. Despite the 98% purity indicated in the reagent characteristics determined by agarose gel electrophoresis, SDS/PAGE denaturing electrophoresis demonstrates [35] protein derivatives with a higher molecular weight. It is thus preferable to determine the purity of BSA preparations via SDS/PAGE. High molecular weight forms are known in commercial preparations Cohn fraction V (Sigma, A7888, Poland) [19]. The separation of the BSA monomer from such high molecular weight protein aggregates has been described, which makes use of fractionation in a column packed with the dextran gel Sephadex G-200 (Pharmacia, Sweden), equilibrated with PBS (phosphate-buffered saline) pH 7.5 containing 0.02% $NaN_3$ at room temperature [19]. However, 0.25% saccharide contamination was demonstrated [19]. Therefore, the use of Sephadex G-200 as a molecular sieve is not preferable, because the contamination level of the isolated protein with saccharides grows due to the participation of dextran molecules from the gel, protein modification and other reactions. According to earlier reports, BSA may be modified by dextran via the Maillard reaction and form BSA-dextran conjugates of various molecular weights [36]. The presence of saccharide conjugates and high-molecular mass derivatives in available commercial BSA preparations excludes them from use in primary research in molecular biology. For this reason, it is necessary to design a simple method of obtaining BSA from commercial preparations, in monomeric form and lacking saccharide inclusions. Unexpectedly, the aforementioned problem was solved by the present invention.

The first subject the present invention is an analytically pure monomeric bovine serum albumin, which does not contain saccharide contaminants determined electrophoretically via SDS/PAGE in a 12% separating gel. By analytically pure, we mean the absence of saccharide contaminants, as detected by the aforementioned method. Equally preferably, pure monomeric bovine serum albumin according to the present invention is characterised in that the molecular diameter is substantially 7 nm.

The second subject of the present invention is a method of isolating monomeric serum albumin characterised in that it encompasses:

a) preparation of a sample of BSA, b) chromatographic purification of the obtained sample from stage (a) on a resin, preferably HW-55, equilibrated with an equilibration buffer, preferably 0.1 M acetate buffer, pH 5.65 containing 1% n-butanol. Equally preferably, a method according to the present invention is characterised in that stage a) encompasses the removal of hydrophobic ligands, preferably via passing the sample through charcoal. Equally preferably, a method according to the present invention is characterised in that the purification during stage b) occurs at room temperature at a rate of 1.2 ml/ 10 min.

The third subject of the present invention is a method of identifying albumin characterised in that it encompasses determining the diameter of protein molecules using dynamic light dispersion in fractions obtained using the method according to the present invention, wherein the monomeric fractions are those baring molecules substantially with a diameter of 7 nm.

The main advantage of a monomeric fraction of BSA obtained according to the present invention is the homogeneity of the resulting protein and the absence of saccharide contaminants. Homogeneity of the resulting protein determined using the conventional denaturing electrophoresis method was additionally confirmed by determining the protein molecule diameters in fractions obtained from the HW-55S column via dynamic light scattering (DLS) [37]. The values of molecule diameters confirmed the presence of monomeric BSA and corresponded with previous literature data [38]. The identification of the resulting BSA monomer via DLS is preferable due to the possibility of simultaneous determination of homogeneity (%) of the resulting albumin fractions. The definitive advantage is the decreased time in comparison to a conventional purity analysis via SDS/PAGE. It is preferable to use the acid phenol method [39] to determine the total saccharide content of the obtained fraction of BSA monomer. The absence of saccharide contaminants in the obtained preparation is evidence of the advantage of the method being the subject of the present invention, over two other methods of isolating monomeric bovine albumin, described in the examples as disadvantageous. An additional advantage of isolating the BSA monomer from commercial preparations according to the present invention is the simple procedure and low cost.

Figure 2:
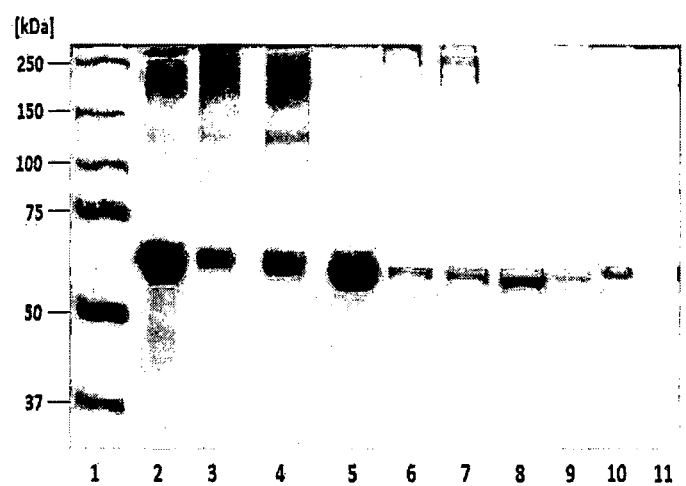
Figure 4:
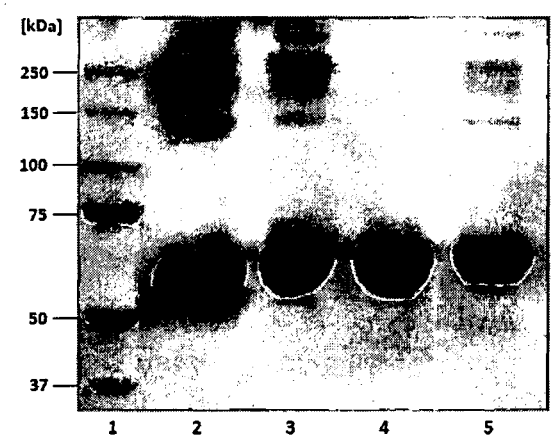
Figure 3:
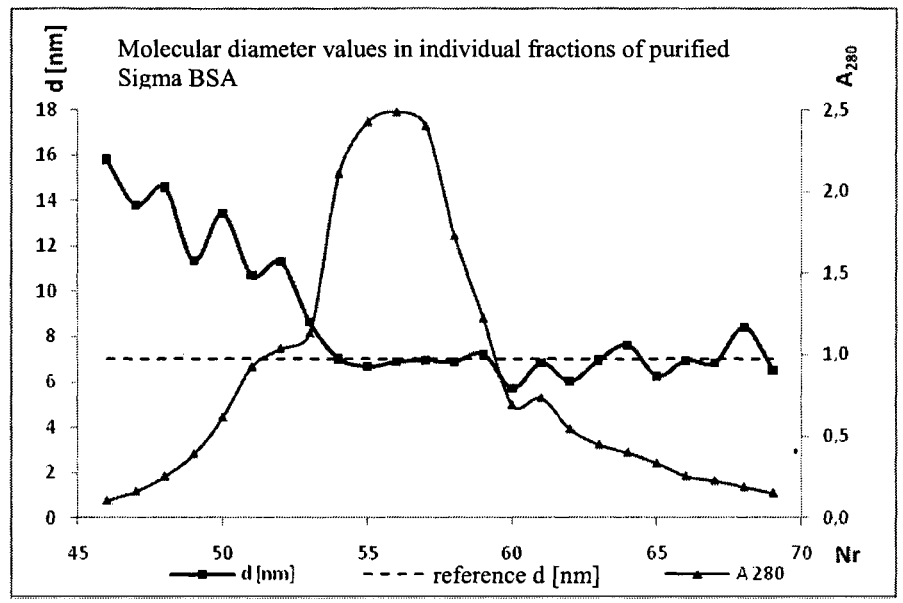
Figure 3:
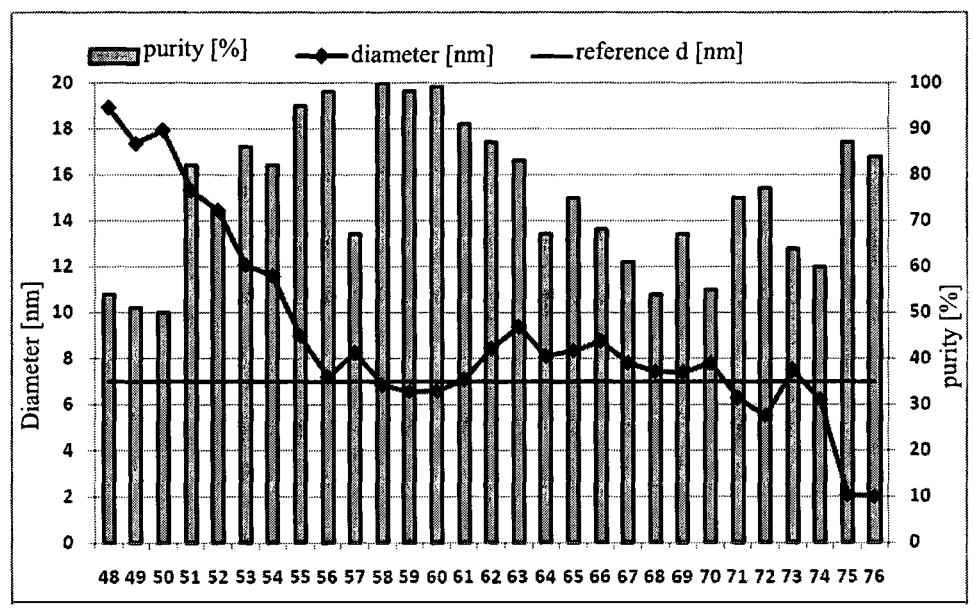

Example embodiments of the present invention are shown in the illustration, wherein FIG. 1 represents an elution profile of commercial BSA (Sigma-Aldrich A3294): A) following chromatography on HW-55S; B) following gel filtration on Sephadex G-200; C) anion exchange chromatography on DEAE-Sephadex A-50, FIG. 2 represents SDS/PAGE analysis of BSA samples in a 12% separating gel, wherein: lane 1) protein molecular weight marker standards; 2) 6 µg commercial BSA sample (Sigma-Aldrich A3294); lanes 3) and 4), respectively: 3 µg fractions A and B obtained following HW-55S chromatography; lane 5) 6 µg fractions C eluted from the HW-55S column; lanes 6) and 7) respectively, 2 µg of fractions A and B following a Sephadex G-200 column; lane 8) 3 µg fraction C obtained following fractionation in Sephadex G-200; lanes 9), 10) and 11) respectively, following 2 µg fractions 90-100, 115-123 and 124-150 following purification on DEAE-Sephadex A-50, FIG. 3 represents a dynamic light scattering (DLS) analysis of protein molecule diameters and purity level of albumin bovine obtained via purification chromatography of HW-55S fractions. A) Diameters of protein molecules eluted from the column: the solid line with black triangles denotes absorbance $A_{280}$ as a measure of protein content in the fractions, the solid line with black squares denotes the diameter of molecules, the intermittent line denotes a diameter of 7 nm as a reference for bovine albumin. B) Determination of the purity level (in %) of protein fractions—grey bars of fractions 58-60 represent proteins with the diameter of reference bovine albumin (7 nm) and 100% pure, FIG. 4 represents electrophoresis in a 12% SDS/PAGE gel of BSA modification products with core oligosaccharide (protein modification with a 200-fold molar excess of oligosaccharide over 16 hours at 37° C.): lane 1—protein weight standards; 2—commercial BSA incubated with oligosaccharide; lanes 3 and 4—control samples, respectively, of commercial and monomeric BSA (obtained following purification on a HW 55-S column) incubated under identical conditions without oligosaccharide; lane 5—BSA monomer modified with oligosaccharide.

The subject of the present invention is shown in the example embodiments in terms of examples of the isolation of the BSA monomer from the commercial Sigma-Aldrich preparation (Cohn fraction V, A3294, over 98% pure and determined by the producer using agarose gel electrophoresis). Prior to fractionation chromatography, the samples of commercial BSA were passed through charcoal in order to remove potential hydrophobic ligands, mainly fatty acids. Saccharide levels measured using the acid phenol method in BSA were 0.7% (Tab. 1).

EXAMPLE 1

A method of isolating the BSA monomer from samples of a commercial preparation on a column with HW-55 resin The apex of a column (1.6×100 cm) loaded with HW-55S resin (Toyopearl, Tosh Bioscience) equilibrated with 0.1 M acetate buffer pH 5.65 containing 1% n-butanol was loaded with 60 mg commercial BSA. 12% SDS/PAGE analysis confirmed the polydispersion of the commercial preparation: in addition to monomeric albumin with a molecular weight of 69 kDa we observed the presence of aggregates with Mw of 200 kDa and lower weight derivatives (FIG. 2, lane 2). Protein was eluted from the column with equilibration buffer, at room temperature, at a rate of 1.2 ml/10 min. In fractions eluted from the column in peak D (FIG. 1A), there was a homogenous protein with an electrophoretic mobility corresponding to albumin (molecular mass of 69 kDa), which was demonstrated using electrophoretic analysis in 12% SDS/PAGE (FIG. 2, lane 5). The isolated protein was identified as albumin using a new method, by determining the diameter of protein molecules using dynamic light scattering (DLS) in a Zeta-seizer NanoZS analyzer (Malvern, GB). The molecular diameter observed in fractions 53-58 collected from the HW-55S column was 7 nm (FIG. 3, solid line with black squares), which corresponds to literature data for monomeric BSA [39].

The phenol method analysis of total saccharide content in the obtained fractions demonstrated the lack of saccharide contaminants (Tab. 1).

EXAMPLE 2

A method of isolating the BSA monomer from samples of a commercial preparation using molecular sieving in Sephadex G-200 polydextran gel (Amersham Pharmacia).

A 50 mg sample of commercial BSA was loaded onto the apex of a column of Sephadex G-200 equilibrated with PBS (phosphate-buffered saline) pH 7.5 containing 0.02% $NaN_3$. Protein elution was performed with equilibration buffer at room temperature, at a rate of 1.2 ml/15 min. The non-homogeneity of commercial BSA is evidenced by the fact that the albumin fractions eluted in three protein peaks (FIG. 1B). SDS/PAGE analysis demonstrated that the BSA was found in peak C (FIG. 2, lane 8). It constituted 60% of the mass of the loaded commercial preparation. The saccharide content detected using the phenol method is about 1% of saccharide and in the resulting monomeric protein it was slightly higher than in the commercial sample (Tab. 1), which suggests that this is the result of dextran contaminants. This is evidence of the inapplicability of filtering through Sephadex G-200 gel to obtain pure BSA monomer.

EXAMPLE 3

A method of isolating of BSA monomer from samples of commercial preparation using ion exchange chromatography on DEAE-Sephadex A-50 anionic gel (Amersham Pharmacia).

A column (3×25 cm) packed with the anionic gel DEAE-Sephadex A-50 and equilibrated with 0.02 M phosphate buffer pH 8.0 was loaded with 600 mg commercial BSA dissolved in 1 ml equilibration buffer. Albumin mixed with the ion exchanger was eluted with a concentration gradient of 0.02-.0.3 M phosphate pH 8.0. The protein eluted at a rate of 1 ml/20 min, at the lower range of elution buffer concentration in peak A, (FIG. 1C) was electrophoretically homogenous (FIG. 2, lane 9). 12% SDS/PAGE analysis indicated that high-molecular weight aggregates of the commercial protein samples eluted at higher phosphate gradient concentrations, in peak C (FIG. 2, lane 11). Due likely to the non-enzymatic modification of proteins by carbohydrates (glycation), the formed protein derivatives have a more negative charge (available basic amino-acid residues are blocked by a glycating agent) and bind the anionic gel more strongly.

The total saccharide content in the fractions collected in peak A, determined using the phenol method was 0.9% (Tab. 1). For this reason, the use of an anion exchanger such as DEAE-Sephadex is not useful for obtaining pure BSA monomer.

EXAMPLE 4

The significance of the present invention is shown in an example use of BSA monomer in forming glycoconjugates with the core oligosaccharide of the lipopolysaccharide of *Shigella sonnei* PhII.

A sample of commercial BSA and monomeric albumin (obtained following fractionation on HW-55S) were incubated with bacterial oligosaccharide (the molar ratio of protein to oligosaccharide was 1:200) at a temperature of 37° C. for 16 hours. The modification conditions were selected based on earlier reports [22,23] and the reaction products were analysed electrophoretically via SDS/PAGE on a 12% separating gel. In the BSA monomer sample incubated with oligosaccharide we observe glycoconjugates, whereas a control sample without oligosaccharide does not generate such products (FIG. 4, lanes 5 and 4 respectively). As a result of the modification of the commercial BSA preparation, we obtained glycoconjugates with a Mw in the range 130-530 kDa, visible in lane 2 in FIG. 4. A similar composition, though less intense, was observed in the control commercial sample not treated with oligosaccharide (FIG. 4, lane 3). Thus, the use of commercial BSA as a model protein in the evaluation of protein modification should be excluded due to an extensive bias in the results. Only a pure BSA makes it possible to obtain proper results; and for this reason it is preferable to use HW-55S resin for its isolation from a commercial preparation.

TABLE 1

Total saccharide content in BSA samples

| Sample | Saccharide content (%) |
| --- | --- |
| Commercial BSA (Sigma-Aldrich A3294) | 0.7 |
| Monomeric BSA following Sephadex G-200 | 1.0 |
| Monomeric BSA following DEAE Sephadex | 0.9 |
| Monomeric BSA following HW-55S | 0 |

References

[1] T. Chakraborty, I. Chakraborty, S. P. Moulik, S. Ghosh, Physicochemical and conformational studies on BSA-surfactant interaction in aqueous medium, Langmuir 25 (2009) 3062-3074.

[2] H. Yoneyama, M. Yamashita, S. Kasai, K. Kawase, R. Ueno, H. Ito, T. Ouchi, Terahertz spectroscopy of native-conformational and thermally denatured bovine serum albumin (BSA), Phys. Med. Biol. 53 (2008) 3543-3549.

[3] L. Jin, Y. X. Yu, G. H. Gao, A molecular-thermodynamic model for the interactions between globular proteins in aqueous solutions: applications to bovine serum albumin (BSA), lysozyme, alpha-chymotrypsin, and immune-gamma-globulins (IgG) solutions, J. Colloid Interface Sci. 304 (2006) 77-83.

[4] A. E. Alegria, P. Sanchez-Cruz, A. Kumar, C. Garcia, F. A. Gonzalez, A. Orellano, B. Zayas, M. Gordializa, Thiols oxidation and covalent binding of BSA by cyclolignanic quinones are enhanced by the magnesium cation, Free Radical Res. 42 (2008) 70-81.

[5] J. R. Brown, Albumin structure, function and uses (Rosenover, V. M., Oratz, M., Rothschild, M. A. Eds.), Pergamon Press, (1977) Oxford, UK.

[6] Q. Pan, M. Zhao, S. Liu, Combination of on-chip field amplification and bovine serum albumin sweeping for ultrasensitive detection of green fluorescent protein, Anal. Chem. 81 (2009) 5333-5341.

[7] J. H. Wang, H. Q. Wang, H. L. Zhang, X. Q. Li., X. F. Hua, Y. C. Cao, Z. L. Huang, Y. D. Zhao, Purification of denatured bovine serum albumin coated CdTe quantum dots for sensitive detection of silver(I) ions, Anal. Bioanal. Chem. 388 (2007) 969-974.

[8] E. Alarcón, A. M. Edwards, A. M. Garcia, M. Muñoz, A. Aspée, C. D. Borsarelli, F. A. Lissi, Photophysics and photochemistry of zinc phthalocyanine/bovine serum albumin adducts, Photochem. Photobiol. Sci. 8 (2009) 255-263.

[9] J. Kang, O. Lambert, M. Ausborn, S. P. Schwenderman. Stability of proteins encapsulated in injectable and biodegradable poly(lactide-co-glycolide)-glucose millicylinders, Int. J. Pharm. 357 (2008) 235-243.

[10] J. Li, P. Yao, Self-assembly of ibuprofen and bovine serum albumin-dextran conjugates leading to effective loading of the drug, Langmuir 25 (2009) 6385-6391.

[11] N. Seedher, S. Bhatia, Complexation of cox-2 inhibitors with bovine serum albumin: interaction mechanism, Pharm. Dev. Technol 14((2009) 343-349.

[12] L. Yang, F. Cui, D. Cun, A. Tao, K. Shi, W. Lin, Preparation, characterization and biodistribution of the lactone form of 10-hydroxycamptothecin (HCPT)-loaded bovine serum albumin (BSA) nanoparticles, Int. J. Pharm. 340 (2007) 163-172.

[13] P. Branaa, J. Naar, M. Chinain, S. Pauillac, Preparation and characterization of domoic acid-protein conjugates using small amount of toxin in a reversed micellar medium: application in a competitive enzyme-linked immunosorbent assay, Bioconjug. Chem. 10 (1999), 1137-1142.

[14] J. Das Sarma, C. Duttagupta, E. Ali, T. K. Dhar, T. K. Antibody to folic acid: increased specificity and sensitivity In ELISA by using ε-aminocaproic acid modified BSA as the carrier protein, J. Immunol. Methods 184 (1995) 1-6.

[15] E. Paulovicová, J. Korcova, P. Farkas, S. Bystrický, Immunological efficacy of glycoconjugates derived from Vibrio cholerae O1 serotype Ogawa detoxified LPS in mice, J Med Microbiol. 59 (2010), 1440-1448.

[16] P. Farkas, J. Korcová, J. Kronek, S. Bystrický, Preparation of synthetic polyoxazoline based carrier and Vibrio cholerae O-specific polysaccharide conjugate vaccine, Eur J Med Chem. 45 (2010) 795-799.

[17] J. B. Robbins, J. Kübler-Kielb, E. Vinogradov, C. Mocca, V. Pozsgay, J. Shiloach, R.

Schneerson, Synthesis, characterization, and immunogenicity in mice of Shigella sonnei O-specific oligosaccharide-core-protein conjugates, Proc Natl Acad Sci USA. 106 (2009) 7974-7978.

[18] J. F. Vljegenthart, Carbohydrate based vaccines, FEBS Lett. 580 (2006) 2945-2950.

[19] M. Staniszewska, S. Jarosz, M. Jon, A. Gamian, Advanced glycation end-products prepared in solution under high pressure contain epitopes distinct from those formed in the dry reaction at high temperature, Arch. Immunol. Ther. Exp. 53 (2005) 71-78.

[20] S. Thorpe, J. W. Baynes, Maillard reaction products in tissue proteins: new products and new perspectives, Amino Acids 25 (2003) 275-281.

[21] P. Ulrich, A. Cerami, Protein glycation, diabetes, and aging, Recent Prog. Horm. Res. 56 (2001) 1-21.

[22] J. Pietkiewicz, A. Gamian, M. Staniszewska, R. Danielewicz, Inhibition of human muscle-specific enolase by methylglyoxal and irreversible formation of advanced glycation end products, J. Enyme Inhib. Med. Chem.24 (2009) 356-364.

[23] J. Pietkiewicz, A. Bronowicka-Szydelko, K. Dzierzba, R. Danielewicz A. Gamian, Glycation of the muscle-specific enolase by reactive carbonyls: effect of temperature and the protection role of carnosine, pirydoxamine and phosphatidylserine, Prot J. in press, (2011) DOI: 10.1007/s10930-011-9307-3.

[24] A. I. Ledesma-Osuna, G. Ramos-Clamont, L. Vázquez-Moreno, Characterization of bovine serum albumin glycated with glucose, galactose and lactose, Acta Biochim. Pol. 55 (2008) 491-497.

[25] U. Kańska, J. Boratyński, Thermal glycation of proteins by D-glucose and D-fructose, Arch. Immunol. Ther. Exp. 50 (2002) 61-66.

[26] J. Boratyński, R. Roy, High temperature conjugation of proteins with carbohydrates, Glycoconj. J. 15 (1998) 131-138.

[27] C. P. Quan, S. Wu, N. Dasovich, C. Hsu, T. Patapaff, E, Canova-Davis, Susceptibility of rhDNase to glycation in the dry-powder state, Anal. Chem. 71 (1999) 4445-4454.

[28] S. Fisher, J. Hoernschemeyer, H. C. Mahler, Glycation during storage and administration of monoclonal antibody formulations, Eur. J. Pharm. Biopharm. 70 (2008) 42-50.

[29] D. J. S. Hinton, J. M. Ames, Site specificity of glycation and carboxymethylation of bovine serum albumin by fructose, Amino Acids 30 (2006) 425-433.

[30] T. J. Wu, M. C. Tu, P. Zhung, P, Advanced glycation end product (AGE): characterization of the products from the reaction between D-glucose and serum albumin, J. Clin. Lab. Anal. 10 (1996) 21-34.

[31] J. Rangsansarid, N. Cheetangdee, N. Kinoshita, K. Fukuda, Bovine serum albumin-sugar conjugates through the Maillard reaction: effects on interfacial behavior and emulsifying ability. J. Oleo Sci. 57 (2008) 539-547.

[32] F. K. Yeboah, Z. Alli, V. A. Yaylayan, Reactivities of D-glucose and D-fructose during glycation of bovine serum albumin, J. Agric. Food Chem. 47 (1999) 3164-3172.

[33] I. Bednarz-Misa, J. Pietkiewicz, T. Banal, A. Gamian. Enolase from *Klebsiella pneumoniae* and human muscle cells. I. Purification and comparative molecular studies, Adv Clin Exp Med. 18 (2009) 71-78

[34] D. Witkowska, J. Pietkiewicz, B. Szostko, R. Danielewicz, L. Maslowski, A. Gamian, Antibodies against human muscle enolase recognize a 45-kDa bacterial cell wall outer membrane enolase-like protein, FEMS Immunol Med. Microbiol. 42 (2005) 53-62.

[35] U. K. Laemmli, Cleavage of structural proteins during the assembly of the head of bacteriophage T4, Nature (London) 227 (1970) 680-685.

[36] S. H. Jung, S. J. Choi, H. J. Kim T. W. Moon, Molecular characteristics of bovine serum albumin-dextran conjugates, Biosci. Biotechnol. Biochem. 70 (2006) 2064-2070.

[37] T. Hushcha, A. Luik, Y. Naboka, Conformation changes of albumin in its interaction with physiologically active compounds as studied by quasi-elastic light scattering spectroscopy and ultrasonic method, Talanta, 53 (2000) 29-34.

[38] G. Navarra, A. Tinti, M. Leone, V. Militello, A. Torreggiani, Influence of metal ions on thermal aggregation of bovine serum albumin: aggregation kinetics and structural changes, J Inorg Biochem. 103 (2009) 1729-3178.

[39] M. Dubois, K. A. Gilles, J. K. Hamilton, P. A. Rebers, F. Smith, Colorimetric method for determination of sugar and related substances, Anal. Chem. 28 (1956) 350-356.

The invention claimed is:

1. A method of obtaining analytically pure monomeric bovine serum albumin devoid of high molecule weight protein aggregates and saccharide contaminates comprising:
   a) obtaining a bovine serum albumin preparation, and
   b) purifying the preparation obtained in step a) by performing chromatography on a HW-55 resin equilibration with a buffer, so as to obtain analytically puer monomeric bovine serum albumin devoid of high molecular weight protein aggregates and saccharide contaminants.

2. The method according to claim 1, wherein step a) includes removing hydrophobic ligands from the bovine serum albumin.

3. The method according to claim 1, wherein the chromatograpy of step b) is performed at room temperature at a rate of 1.2 ml/10 min.

4. The method of claim 1, further comprising step c) after step b), wherein step c) comprises:
   c) performing dynamic light scattering to determine the diameter of bovine serum albumin molecules in the sample obtained from the chromatography of step b), wherein the presence of bovine serum albumin molecules with a diameter of about 7 nm indicate the sample contains analytically pure monomeric bovine serum albumin devoid of high molecular weight protein aggregates and saccharide contaminants.

5. The method of claim 1, wherein the buffer of step b) is 0.1 M acetate buffer, at pH 5.65, containing 1% n-butanol.

6. The method of claim 2, wherein the hydrophobic ligands are removed by passing the bovine serum albumin through charcoal.

7. The method of claim 1, wherein the monomeric bovine serum albumin is analytically pure and devoid of high molecular weight protein aggregates and saccharide contaminants as determined electrophoretically by SDS/PAGE in a 12% separating gel.

8. The method of claim 7, wherein the monomeric bovine serum albumin is devoid of saccharide contaminants as determined by phenol method analysis.

* * * * *